United States Patent [19]

Staudenmaier et al.

[11] Patent Number: 5,639,643
[45] Date of Patent: Jun. 17, 1997

[54] PREPARATION OF 3-HYDROXYPHENYLACETIC ACID

[75] Inventors: Horst Ralf Staudenmaier, Limburgerhof; Bernhard Hauer, Fussgoenheim; Wolfgang Ladner, Fussgoenheim; Ursula Mueller, Fussgoenheim; Uwe Pressler, Altrip; Joachim Meyer, Maxdorf, all of Germany

[73] Assignee: BASF Aktiengesellschaft, Ludwigshafen, Germany

[21] Appl. No.: 582,560

[22] Filed: Jan. 2, 1996

Related U.S. Application Data

[63] Continuation of Ser. No. 351,427, filed as PCT/EP93/01484 Jun. 11, 1993, abandoned.

[30] Foreign Application Priority Data

Jun. 20, 1992 [DE] Germany .................. 42 20 241.8

[51] Int. Cl.$^6$ .................................................. C12P 7/42
[52] U.S. Cl. ........................................ 435/146; 435/911
[58] Field of Search .................................. 435/146, 911

[56] References Cited

PUBLICATIONS

Chem Abs 84:40068u (No. 7) (1976) Kohmoto et al.
Chem Abs 86:85840x (No. 13) (1977) Kohmoto et al.
Chem Abs 107:112811z (No. 13) (1987) Iacobellis et al.

Phytopathology vol. 60 Jun. 1970 Kohmoto et al "Pathochemical Studies on Rhizoctonia Disease I. Meta Hydroxlation of Phenylacetic Acid by Rhizoctonia Solani" pp. 1025–1027.

J. of Bacteriology, vol. 141, No. 2, Feb. 1980, pp. 534–543.

Primary Examiner—Herbert J. Lilling
Attorney, Agent, or Firm—Keil & Weinkauf

[57] ABSTRACT

The invention relates to a novel process for preparing 3-hydroxyphenylacetic acid by cultivating a fungus of the genus Rhizoctonia, Ceratobasidium and Pellicularia in the presence of a phenyl compound of the formula I

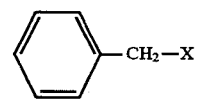

where X is $COOR$, $CH_2OH$, $CH_2NH_2$ or

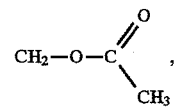

R is methyl, ethyl, hydrogen, sodium, potassium or ammonium.

6 Claims, No Drawings

PREPARATION OF 3-HYDROXYPHENYLACETIC ACID

This application is a continuation of application Ser. No. 08/351,427, filed as PCT/EP93/01484 Jun. 11, 1993 on Dec. 12, 1994 and now abandoned.

The present invention relates to a novel process for preparing 3-hydroxyphenylacetic acid.

It is known that a number of microorganisms is able to hydroxylate phenylacetic acid.

A result of this is, besides various other hydroxylation products, 3-hydroxyphenylacetic acid, but this undergoes further metabolism by the microorganisms (J. J. Anderson et al., J. Bacteriol. 141 (1980) 534–543).

Keisuke Kohmoto et al. (Phytopathology, 60, (1970) 1025–1026) reported that the fungus *Rhizoctonia solani* is able to hydroxylate phenylacetic acid in the meta position. To prepare 3-hydroxyphenylacetic acid, first the fungus was cultured and then the biomass was isolated and incubated with a solution of phenylacetic acid (replacement culture). The maximum concentration of 3-hydroxyphenylacetic acid obtained was 2.5 g/l.

This preparation is unsuitable for an industrial process because of the low concentration of product and the elaborate replacement culture.

It is an object of the present invention to provide a fermentation process for preparing 3-hydroxyphenylacetic acid from phenyl compounds which is straightforward to carry out and gives good yields.

We have found that this object is achieved particularly advantageously by a process in which a fungus of the genus Rhizoctonia, Ceratobasidium or Pellicularia is cultivated in the presence of a conventional nutrient medium to which is added a phenyl compound of the formula I

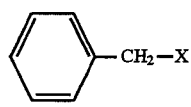

where X is $COOR$, $CH_2OH$, $CH_2NH_2$ or

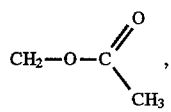

R is methyl, ethyl, hydrogen, sodium, potassium or ammonium.

Fungi of the genera Rhizoctonia, Ceratobasidium and Pellicularia are known (D. L. Hawksworth, B. C. Sutton and G. C. Ainsworth: Ainsworth & Bisby's Dictionary of the Fungi, Seventh Edition, 1983 and issues cited therein).

The species which is particularly suitable for the process according to the invention is *Rhizoctonia solani*.

Nutrient media suitable for cultivating the fungi are those which contain sources of carbon and of nitrogen, inorganic salts and, where appropriate, small amounts of trace elements and vitamins. Sources of nitrogen which can be used are inorganic or organic nitrogen compounds or materials which contain these compounds. Examples are ammonium salts, nitrates, corn steep liquor, yeast autolysate, soybean meal, wheat gluten, yeast extract, yeast, urea and potato protein. Examples of carbon sources which can be used are sugars such as glucose, polyols such as glycerol, or fats such as soybean oil.

Examples of inorganic salts are the salts of calcium, magnesium, manganese, potassium, zinc, copper, iron and other metals. The phosphate ion is a particularly suitable anion in the salts. Growth factors are added where appropriate to the nutrient medium, such as biotin, riboflavin or other vitamins.

Success of the process does not apparently depend on the nature of the nutrient medium.

A phenyl compound is added to the nutrient medium for the process according to the invention. Phenyl compounds which can be used in this process are phenylacetic acid or its salts, especially its alkali metal salts, with the sodium and potassium salts being particularly preferred, or esters, preferably methyl or ethyl phenylacetate. When esters are used as precursors in the process according to the invention, there is not only hydroxylation in the meta position but also cleavage of the ester so that the product is 3-hydroxyphenylacetic acid.

Other suitable phenyl compounds are 2-phenylethanol, 2-phenylethylamine and 2-phenylethyl acetate.

With these substrates in the process according to the invention there is not only hydroxylation in the meta position but also formation of a carboxyl group so that the product is 3-hydroxyphenylacetic acid.

The particularly preferred phenyl compounds are sodium and ammonium phenylacetates.

The phenyl compounds are usually added in amounts such that the concentration is about 1–50 g, preferably 5–30 g, per liter of nutrient medium.

The phenyl compounds can be added to the nutrient medium at the start of cultivation of the fungus or during the cultivation in several portions or continuously.

It is also possible to retain the cultivated fungus after conversion is complete and to cultivate it further in fresh nutrient medium with the phenyl compound.

This type of reuse of the biomass is a particularly advantageous embodiment of the process according to the invention because, for example, this saves the biomass cultivation time.

Cultivation of the fungus does not require any other special conditions. Thus, cultivation can take place at from 20° to 40° C., preferably from 25° to 35° C.

The pH of the fermentation medium is maintained at from 3 to 9 and is advantageously from 4 to 7.

The fermentation times are normally from 1 to 10 days to achieve maximum accumulation of the product in the fermentation medium.

The extent of reaction can easily be determined by taking a sample and analyzing by, for example, gas chromatography.

The invention is illustrated by the following examples.

EXAMPLE 1

Testing of various strains of fungi for conversion of phenylacetic acid into 3-hydroxyphenylacetic acid

| Medium 1 | |
|---|---|
| 10 g/l | glucose |
| 40 g/l | corn steep liquor |
| 1.5 g/l | KH$_2$PO$_4$ |
| 3.6 g/l | K$_2$HPO$_4$ |
| pH 6.8 | |

The phenylacetic acid was dissolved in water with the addition of little dilute NaOH and was sterilized by filtration.

30 ml portions of medium 1 containing 1 g/l phenylacetic acid were introduced into sterile 250 ml Erlenmeyer flasks with a baffle. The flasks were each inoculated with a 0.5×0.5 cm piece of agar which had been punched out of an agar plate on which a particular strain had been grown. The flasks were shaken at 180 rpm and 25° C. After 3 and 7 days, 1 ml of the culture supernatant was removed, mixed with 100 µl of 5N hydrochloric acid and 800 µl of ethyl acetate and agitated vigorously for 15 s. 700 µl of the ethyl acetate phase were removed and evaporated at 50° C. under a gentle stream of nitrogen. The residue was dissolved in 70 µl of ethyl acetate, and 50 µl of this was transferred into a gas chromatography sample vessel. To this were added 50 µl of N-methyl-N-trimethylsilyltrifluoroacetamide (MSTFA) and mixed. The samples were investigated by gas chromatography with an authentic sample of 3-hydroxyphenylacetic acid for comparison.

The results are compiled in the table.

TABLE

Conversion of phenylacetic acid to 3-hydroxyphenylacetic acid

| Strain | % conversion after | |
|---|---|---|
| | 3 days | 7 days |
| Rhizoctonia solani LU 6467 | 50.0 | 11.9* |
| Rh. solani LU 6464 | 0.0 | 0.8 |
| Rh. solani LU 6474 | 12.5 | 6.4* |
| Rh. solani LU 6473 | 22.3 | 55.7 |
| Rh. solani LU 6475 | 14.7 | 80.2 |
| Rh. solani LU 6476 | 48.1 | 28.0* |
| Rh. solani DSM 852 (= ATCC 13250) | 95.5 | 94.3 |
| Rh. solani DSM 63010 (= IBM 11662) | 1.5 | 4.7 |
| Rh. solani DSM 843 (= ATCC 13249) | 51.6 | 63.1 |
| Rh. solani ATCC 10159 | 3.0 | 35.0 |
| Rh. solani ATCC 16116 | 2.0 | 94.0 |
| Rh. solani ATCC 48804 (= CMI 34886) | 57.0 | 79.0 |
| Rh. solani ATCC 62153 | 32.0 | 86.0 |
| Rh. solani ATCC 62154 | 0.0 | 25.0 |
| Rh. solani ATCC 62156 | 80.0 | 97.0 |
| Rh. tuliparum LU 6470 | 0.0 | 1.6 |
| Rh. cerealis LU 6471 | 1.8 | 33.5 |
| Rh. muneratii DSM 903 (= ATCC 13247) | 7.0 | 34.0 |
| Pellicularia filamentosa ATCC 13289 | 2.0 | 61.0 |
| Pellicularia filamentosa ATCC 13290 | 2.0 | 60.0 |
| Ceratobasidium cornigerum CBS 137.82 (= ATCC 13247) | 13.7 | 13.3 |

*Degradation of the product

The strains identified by LU originate from the BASF collection of strains.

EXAMPLE 2

Preparation of 3-hydroxyphenylacetic acid in shaken flasks

A small piece of Rhizoctonia solani (DSM 852) mycelium was used to inoculate a 250 ml Erlenmeyer flask with baffle containing 30 ml of the following medium:

| Medium A: | | |
|---|---|---|
| | 20 g/l | glucose |
| | 5 g/l | yeast extract (DIFCO) |
| | 5 g/l | (NH$_4$)$_2$SO$_4$ |
| | 0.5 g/l | MgSO$_4$ × 7 H$_2$O |
| | 0.05 g/l | MnSO$_4$ × 4 H$_2$O |
| | 2 ml/l | trace element solution |
| | 3 g/l | Carbopol 946 ® (high molecular weight carboxyvinyl polymer) |
| | 1.5 g/l | KH$_2$PO$_4$ |
| | 3.6 g/l | K$_2$HPO$_4$ |
| Trace element solution: | | |
| | 200 mg/l | iron(II) sulfate 1-hydrate |
| | 10 mg/l | zinc(II) sulfate 4-hydrate |
| | 3 mg/l | manganese chloride 4-hydrate |
| | 30 mg/l | boric acid |
| | 20 mg/l | cobalt(II) chloride 6-hydrate |
| | 1 mg/l | copper(II) chloride 2-hydrate |
| | 2 mg/l | nickel(II) chloride 6-hydrate |
| | 3 mg/l | sodium molybdate 2-hydrate |
| | 500 mg/l | ethylenediaminetetraacetic acid (EDTA) |

5 ml of this preculture was used to inoculate a main culture. The main culture medium was 30 ml of medium A without Carbopol but with the addition of 10 g/l phenylacetic acid.

After shaking at 180 rpm and 25° C. for 4 days the phenylacetic acid had been completely converted.

The biomass was then harvested by centrifugation at 4,000 rpm for 5 minutes and used to inoculate fresh medium A containing 20 g/l phenylacetic acid. After conversion of the phenylacetic acid was complete (7 days), this procedure was repeated and the biomass was transferred into fresh medium A containing 30 g/l phenylacetic acid. The phenylacetic acid was completely converted after 10 days. In this way the biomass was reused up to 4 times without detectible loss of activity.

Immediately after completion of the conversion, the cultures contained about 0.5% 2-hydroxyphenylacetic acid and up to 4% 4-hydroxyphenylacetic acid in addition to 3-hydroxyphenylacetic acid. It was possible to reduce the 4-hydroxyphenylacetic acid content to 0–1% by continuing cultivation for one day after the phenylacetic acid had disappeared. This did not affect the concentrations of 2- and 3-hydroxyphenylacetic acid.

EXAMPLE 3

Preparation of 3-hydroxyphenylacetic acid by repeated 10 l fermentations

Medium B:

| | |
|---|---|
| 20 g/l | glucose |
| 7.5 g/l | yeast extract (Fould Springer, 65%) |
| 5 g/l | $(NH_4)_2SO_4$ |
| 0.5 g/l | $MgSO_4 \times 7\ H_2O$ |
| 0.05 g/l | $MnSO_4 \times H_2O$ |
| 2 ml/l | trace element solution |
| 1 g/l | antifoam P 2000 |
| 1.5 g/l | $KH_2PO_4$ |
| 3.6 g/l | $K_2HPO_4$ |

Preculture:

3×330 ml of medium B in round-bottomed flasks with baffle were each inoculated with ⅓ of an agar plate on which DSM 852 had been grown and which had been comminuted with an Ultraturrax, and were shaken at 180 rpm and 25° C. for 3 days.

10 l fermentation:

The preculture was used to inoculate a 10 l fermenter containing medium B plus 10 g/l phenylacetic acid. The fermenter was stirred at 100 rpm and aerated with 0.5 volume of air per reactor volume per minute (vvm). During the fermentation the stirring speed was increased stepwise to 200 rpm and the aeration rate to 1 vvm.

After 88 hours, all the phenylacetic acid had been converted. 9 l of the ferementer contents were drained off and replaced by fresh medium B. The phenylacetic acid concentration was adjusted to 10 g/l by adding a 25% by weight phenylacetic acid solution (in water, adjusted to pH 7 with NaOH).

During the fermentation, 50 g portions of phenylacetic acid were added on 2 occasions. Glucose was replenished if required. After 165 hours all the phenylacetic acid had been converted. The final concentration of 3-hydroxyphenylacetic acid was 26 g/l.

As described above, the fermenter was drained apart from 1 l and replenished with fresh medium B. During fermentation for 165 hours, 4×50 g of phenylacetic acid were added. The final concentration of 3-hydroxyphenylacetic acid was 30.6 g/l.

The fermenter was again pumped empty apart from 1 l.

Isolation of 3-hydroxyphenylacetic acid from the 3rd fermentation broth:

9 liters of fermentation broth were centrifuged (5,000 rpm, 20 min) and the precipitate was washed with 1 l of water and again centrifuged. The supernatant from both centrifugations (about 7 l) was adjusted to pH 2 with $H_2SO_4$ and extracted twice with the same volume of tert-butyl methyl ether. The organic phase was evaporated to dryness to yield 250 g of residue which was 94% pure 3-hydroxyphenylacetic acid.

We claim:

1. A process for preparing 3-hydroxyphenylacetic acid, which comprises cultivating a fungus selected from the group consisting of Rhizoctonia, Ceratobasisium and Pellicularia in a nutrient medium, said nutrient medium comprising, besides sources of carbon and nitrogen and inorganic salts, a phenyl compound of the formula I

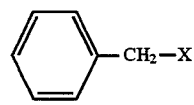   I or salts thereof, where

X is COOR, $CH_2OH$, $CH_2NH_2$ or

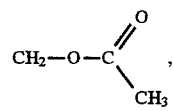

R is methyl, ethyl, hydrogen, sodium, potassium or ammonium;

and recovering said 3-hydroxyphenylacetic acid from said nutrient medium.

2. The process of claim 1, wherein X in the compound of formula I is COOR.

3. The process of claim 2, wherein R in the compound of formula I is hydrogen.

4. The process of claim 1, wherein the fungus used is Rhizoctonia.

5. The process of claim 1, wherein the fungus used is Pellicularia.

6. The process of claim 1, wherein the fungus used is Ceratobasidium.

* * * * *